United States Patent [19]

Nieuwkoop

[11] Plant 4,626

[45] Jan. 20, 1981

[54] ROSE PLANT

[75] Inventor: Jacob Nieuwkoop, De Kwakel, Netherlands

[73] Assignee: Jackson & Perkins Company, Medford, Oreg.

[21] Appl. No.: 51,354

[22] Filed: Jun. 25, 1979

[51] Int. Cl.[3] ..... A01H 5/00

[52] U.S. Cl. ..... Plt./25

[58] Field of Search ..... Plt./25

*Primary Examiner*—Robert E. Bagwill

*Attorney, Agent, or Firm*—Klarquist, Sparkman, Campbell, Leigh, Hall & Whinston

[57] ABSTRACT

This novel rose variety is a mutation of Mercedes and differs therefrom in its blossom colors which are of a more orange red than that of the parent variety.

1 Drawing Figure

DETAILED DESCRIPTION OF INVENTION

The present invention relates to a new and distinct variety of rose plant of the floribunda class, which was discovered by me as a cultivated sport of the hybrid tea rose Mercedes (U.S. Plant Pat. No. 3,724), on a plant grown in The Netherlands.

On Mercedes rose bush, I discovered that flowers on one of the branches were distinctly different from the normal Mercedes in that they were of an orange or salmon shade of red from bud to open flower. Propagation of the budding eyes of this one stem in The Netherlands and at Irvine, Calif. proved that this sport came through on successive propagations.

This new cultivar is substantially identical in all respects to its parent, except for the difference in bud and blossom color noted above. The attached drawing shows the stem, leaves and blossom stages of the new cultivar identified as 678, and the normal blossom and bud colors of Mercedes.

As observed at Irvine, Calif., this new variety as it begins to open, is near Munsell's 2.5 YR 8/10 and in the open blossom, the color is Munsell's 10.0 R 6/10.

Being substantially identical to the parent variety, except for the aforementioned distinctions, reference is made to U.S. Plant Pat. No. 3,724 for a further description of this variety.

I claim:

1. A new and distinct variety of rose plant of the floribunda class, substantially as herein shown and described, characterized particularly as to novelty by the orange or salmon colored hue of bud and bloom on the plant otherwise identical to the variety Mercedes.

* * * * *

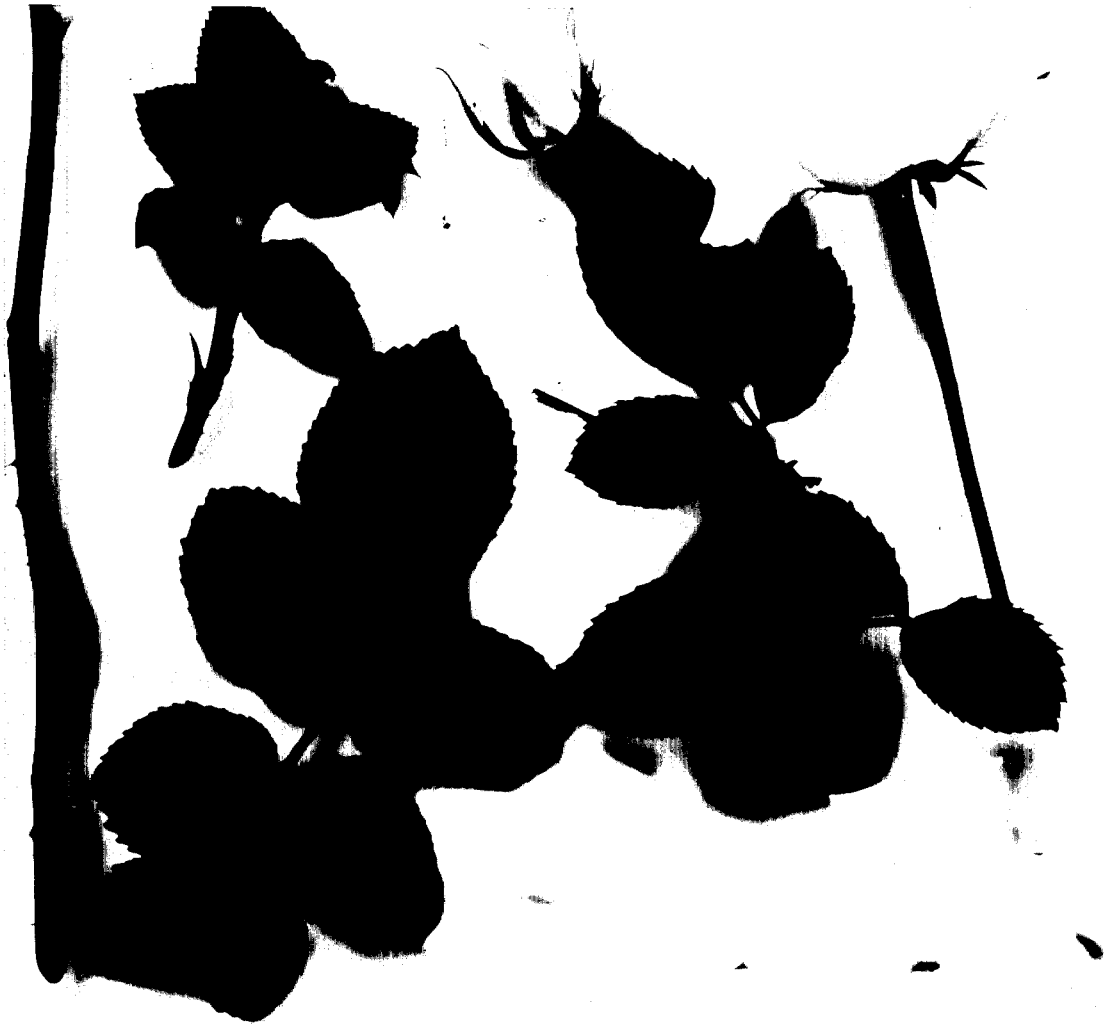
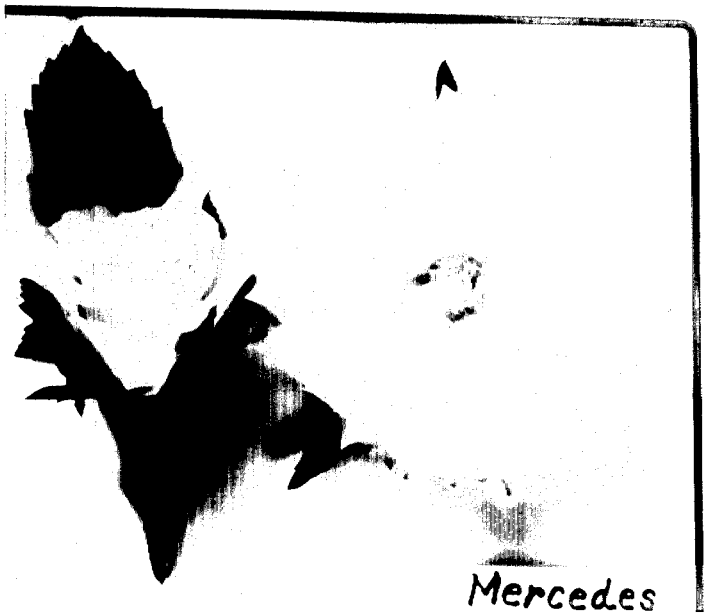
Mercedes 678